(12) United States Patent  
Durrant et al.

(10) Patent No.: US 11,796,109 B2  
(45) Date of Patent: Oct. 24, 2023

(54) CONNECTOR WITH ROTATABLE TUBE

(71) Applicant: CYTIVA US LLC, Marlborough, MA (US)

(72) Inventors: Simon Phillip Durrant, Portsmouth (GB); Danniel Bowdery, Portsmouth (GB); Daniel J. Kesselaar, Portsmouth (GA)

(73) Assignee: Cytiva US LLC, Marlborough, MA (US)

( * ) Notice: Subject to any disclaimer, the term of this patent is extended or adjusted under 35 U.S.C. 154(b) by 0 days.

(21) Appl. No.: 17/563,790

(22) Filed: Dec. 28, 2021

(65) Prior Publication Data

US 2023/0204142 A1 Jun. 29, 2023

(51) Int. Cl.
*F16L 37/53* (2006.01)
*F16L 37/091* (2006.01)

(52) U.S. Cl.
CPC ........... *F16L 37/53* (2013.01); *F16L 37/0915* (2016.05)

(58) Field of Classification Search
CPC ... F16L 37/53; F16L 37/0915; F16L 37/0847; F16L 37/088; F16L 37/096; F16L 37/0985; F16L 37/113; F16L 37/252; F16L 37/24; F16L 37/244; F16L 17/06; A61M 2039/1027; A61M 39/1011; A61M 39/14; A61M 39/165
See application file for complete search history.

(56) References Cited

U.S. PATENT DOCUMENTS

| | | | | |
|---|---|---|---|---|
| 3,603,621 A * | 9/1971 | Parsons | ............... | F16L 37/0985 285/921 |
| 4,524,997 A * | 6/1985 | Ebert | .................... | F16L 37/113 285/380 |
| 4,913,657 A * | 4/1990 | Naito | .................... | F16L 37/113 439/194 |
| 6,325,425 B1 * | 12/2001 | Kierath | ................. | F16L 37/113 285/361 |
| 6,679,529 B2 | 1/2004 | Johnson et al. | | |
| 7,488,446 B2 | 5/2009 | Meyer et al. | | |
| 7,546,857 B2 | 6/2009 | Chadbourne et al. | | |
| 7,631,660 B2 | 12/2009 | deCler et al. | | |
| 7,862,090 B1 * | 1/2011 | Foreman | ............... | F16L 37/244 285/280 |
| 9,423,062 B2 * | 8/2016 | Steele | ................ | A61M 39/1011 |
| 9,726,308 B2 | 8/2017 | Williams et al. | | |
| 10,234,042 B2 | 3/2019 | Bowdery | | |
| 10,247,342 B2 * | 4/2019 | Kesselaar | .......... | A61M 39/1011 |

(Continued)

FOREIGN PATENT DOCUMENTS

CN 107709866 A 2/2018
EP 2 669 564 A2 12/2013

(Continued)

OTHER PUBLICATIONS

European Patent Office, Extended European Search Report issued in European Patent Application No. 22207267.0, dated May 10, 2023.

*Primary Examiner* — David Bochna
(74) *Attorney, Agent, or Firm* — Leydig, Voit & Mayer, Ltd.

(57) ABSTRACT

A connector is provided comprising a hollow connector body having a central aperture and a hollow tube that is rotatable within the central aperture without rotating the hollow connector body.

8 Claims, 14 Drawing Sheets

(56) References Cited

U.S. PATENT DOCUMENTS

| | | |
|---|---|---|
| 10,946,183 B2 | 3/2021 | Faldt et al. |
| 2005/0167980 A1* | 8/2005 | Bauer ................. F16L 37/0985 285/308 |
| 2006/0273587 A1* | 12/2006 | Ambrosi ............... F16L 37/252 285/401 |
| 2010/0230961 A1* | 9/2010 | Johnson .............. F16L 37/0985 285/352 |
| 2015/0048613 A1* | 2/2015 | Bauer ................... F16L 37/252 285/192 |
| 2017/0299099 A1 | 10/2017 | Williams et al. |
| 2018/0296817 A1 | 10/2018 | Burdge |
| 2019/0298985 A1 | 10/2019 | Truong et al. |
| 2020/0032922 A1 | 1/2020 | Wilhelm |

FOREIGN PATENT DOCUMENTS

| | | |
|---|---|---|
| EP | 3 225 895 A1 | 10/2017 |
| WO | WO 2009/097321 A1 | 8/2009 |

* cited by examiner

CONNECTOR WITH ROTATABLE TUBE

BACKGROUND OF THE INVENTION

Connectors for use in fluid processing systems and fluid processing (such as liquid products used in the pharmaceutical and biotechnological industries) are known. However, there is a need for improved connectors. The present invention provides for ameliorating at least some of the disadvantages of the prior art. These and other advantages of the present invention will be apparent from the description as set forth below.

BRIEF SUMMARY OF THE INVENTION

An aspect of the invention provides a connector comprising (a) a hollow connector body having a bottom face and an inner wall forming a central aperture, the central aperture passing through the bottom face; the inner wall having at least two resilient fingers, each of the at least two resilient fingers having an upper tip with an inwardly facing projection; and (b) a hollow tube retained in the central aperture, the hollow tube having a first open end, a second open end, and a longitudinal axis, the second end having a lower face including a central aperture and including a lower face annular groove including a resilient deformable annular seal arranged in the lower face annular groove surrounding the central aperture; the hollow tube including at least upper, middle, and lower grooves spaced apart along the longitudinal axis, the lower groove including a second resilient annular seal arranged in the lower groove, sealing against a portion of the inner wall of the hollow connector body; wherein the inwardly facing projections of the at least two resilient fingers of the hollow connector body are inserted in the upper groove of the hollow tube such that the hollow tube is rotatable within the central aperture without rotating the hollow connector body.

In accordance with another aspect of the invention, a connector assembly is provided, comprising an aspect of the connector, further comprising a locking mechanism, a removable anti-actuation subassembly of an anti-actuation assembly, and a removable cap.

In accordance with yet another aspect of the invention, a method for making fluid connections is provided, the method comprising (a) placing a bottom face of a first hollow connector body of a first connector assembly comprising a first rotatable hollow tube including a resilient deformable annular seal arranged in an annular groove, wherein the first rotatable hollow tube is retained in a central aperture of the first hollow connector body, wherein the bottom face of the first hollow connector body comprises a first locking mechanism integrally formed with the bottom face of the first hollow connector body, the first locking mechanism comprising at least one lug including a slot, and at least one ramp, in contact with a bottom face of a second hollow connector body of a second connector assembly comprising a second rotatable hollow tube including a second resilient deformable annular seal arranged in an annular groove, wherein the second rotatable hollow tube is retained in a central aperture of the second hollow connector body, wherein the bottom face of the second hollow connector body comprises a second locking mechanism integrally formed with the bottom face of the second hollow connector body, the second locking mechanism comprising at least one lug including a slot, and at least one ramp; in a first position; and (b) twisting the first hollow connector body and/or the second hollow connector body such that the first locking mechanism engages with the second locking mechanism, the first resilient deformable seal seals against the first hollow tube in the annular groove surrounding the central aperture of the first follow connector body, and the second resilient deformable seal seals against the second hollow tube in the annular groove surrounding the central aperture of the second hollow connector body, in a second position, the second position comprising an actuation position.

BRIEF DESCRIPTION OF THE SEVERAL VIEWS OF THE DRAWING(S)

Figure 5A:
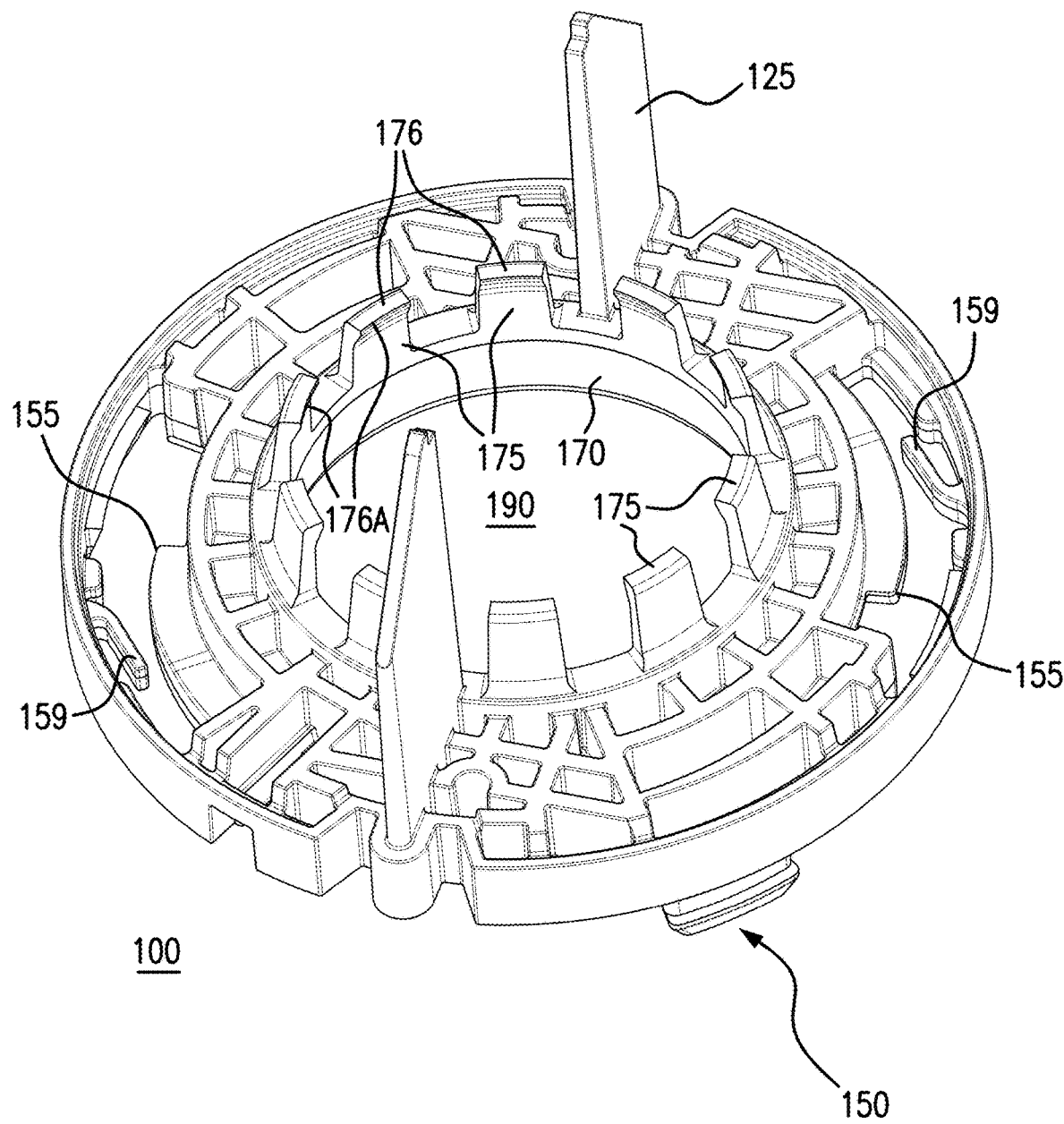
Figure 5B:
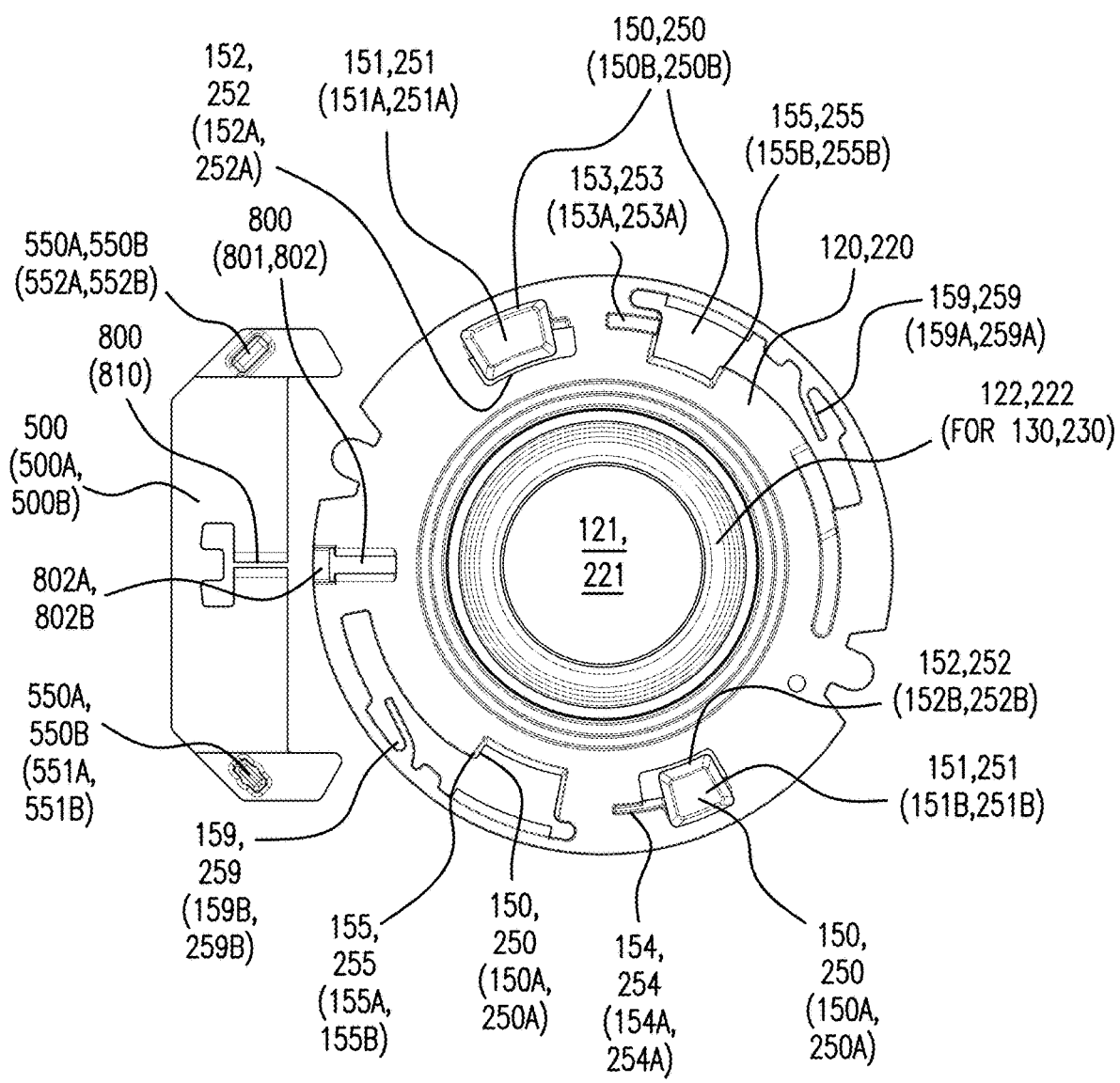
Figure 5C:
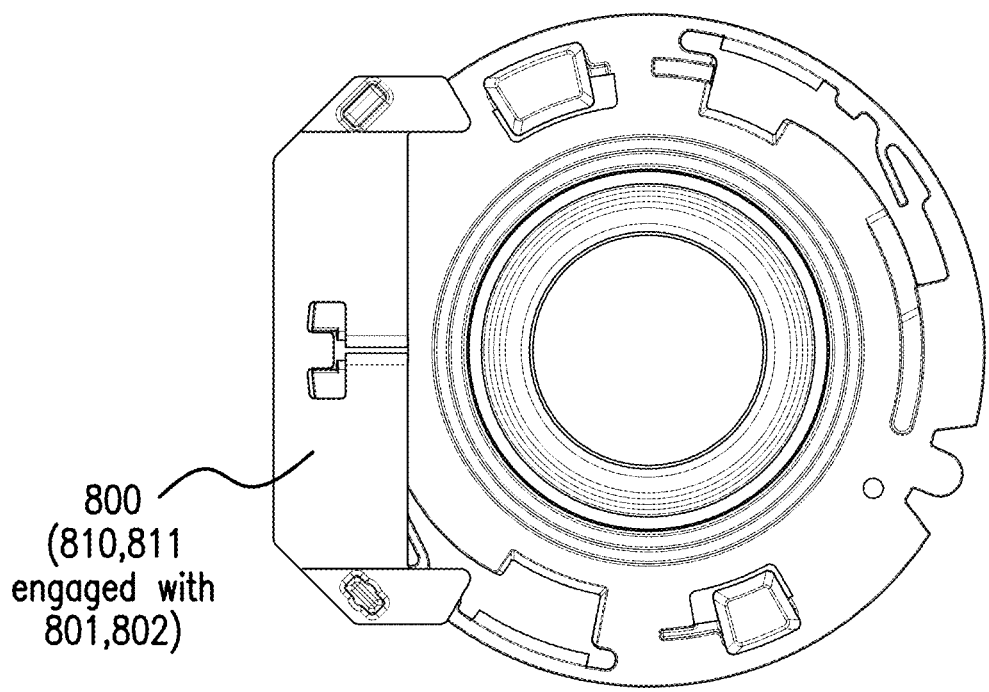

FIG. 5A is a drawing showing a top perspective view of the hollow connector body; FIG. 5B is a drawing showing a bottom end view of the hollow connector body, also showing a groove for containing a resilient deformable annular seal; a locking mechanism integrally formed with the hollow connector body, the locking mechanism comprising lugs including slots, and ramps; and a component of an alignment arrangement for engagement with the anti-actuation assembly, wherein the component comprises at least one recess (illustrated as two recesses) in the first end of a hollow connector body; FIG. 5C is a drawing showing the anti-actuation tab engaged with the first end of a hollow connector body via the alignment arrangement.

Figure 1:
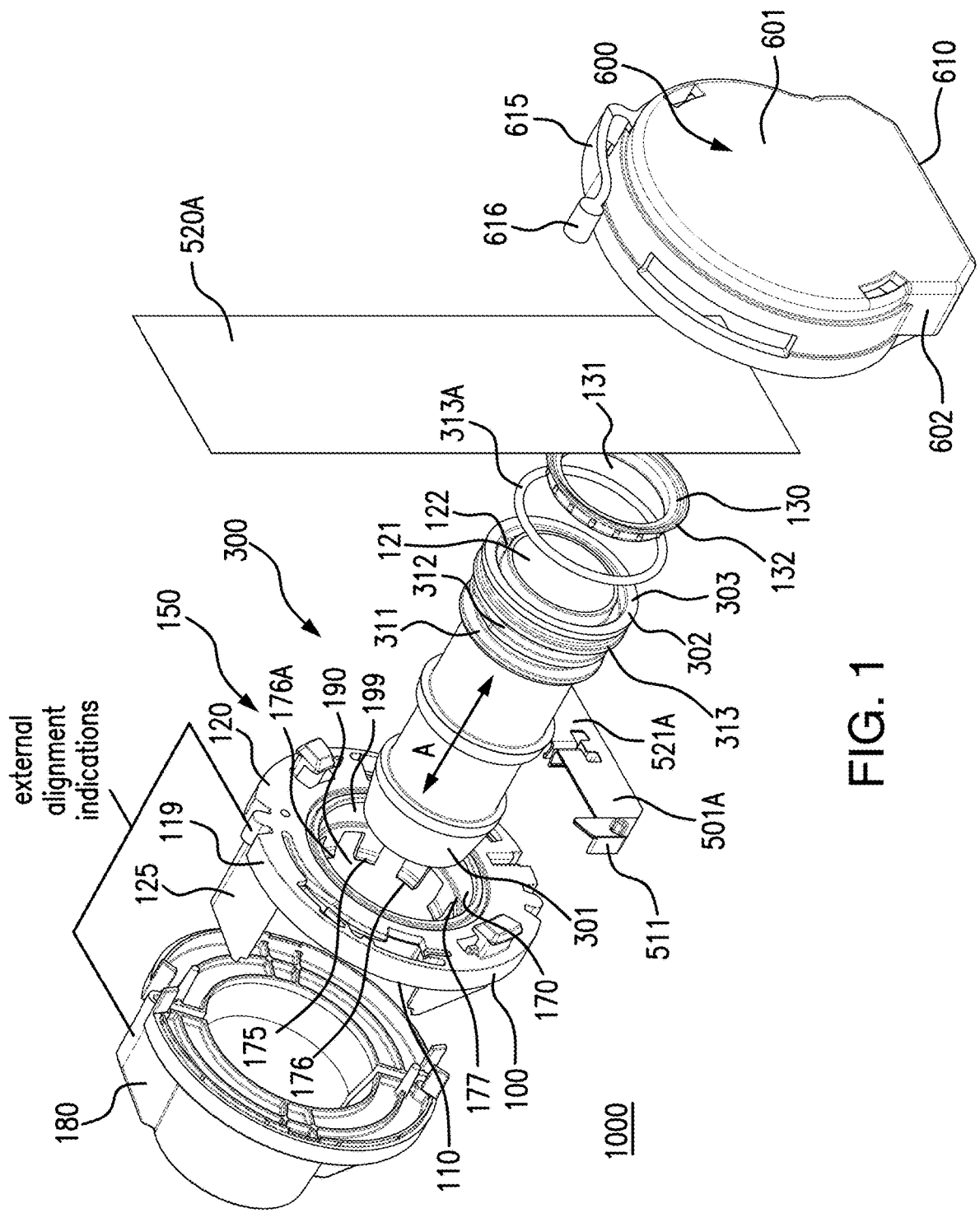
FIG. 1 is a drawing showing an exploded view of a connector assembly comprising a connector comprising a hollow connector body and a rotatable hollow tube according to an aspect of the invention, wherein the connector assembly further comprises a locking mechanism, a removable anti-actuation subassembly of an anti-actuation assembly, and a removable cap.
Figure 2A:
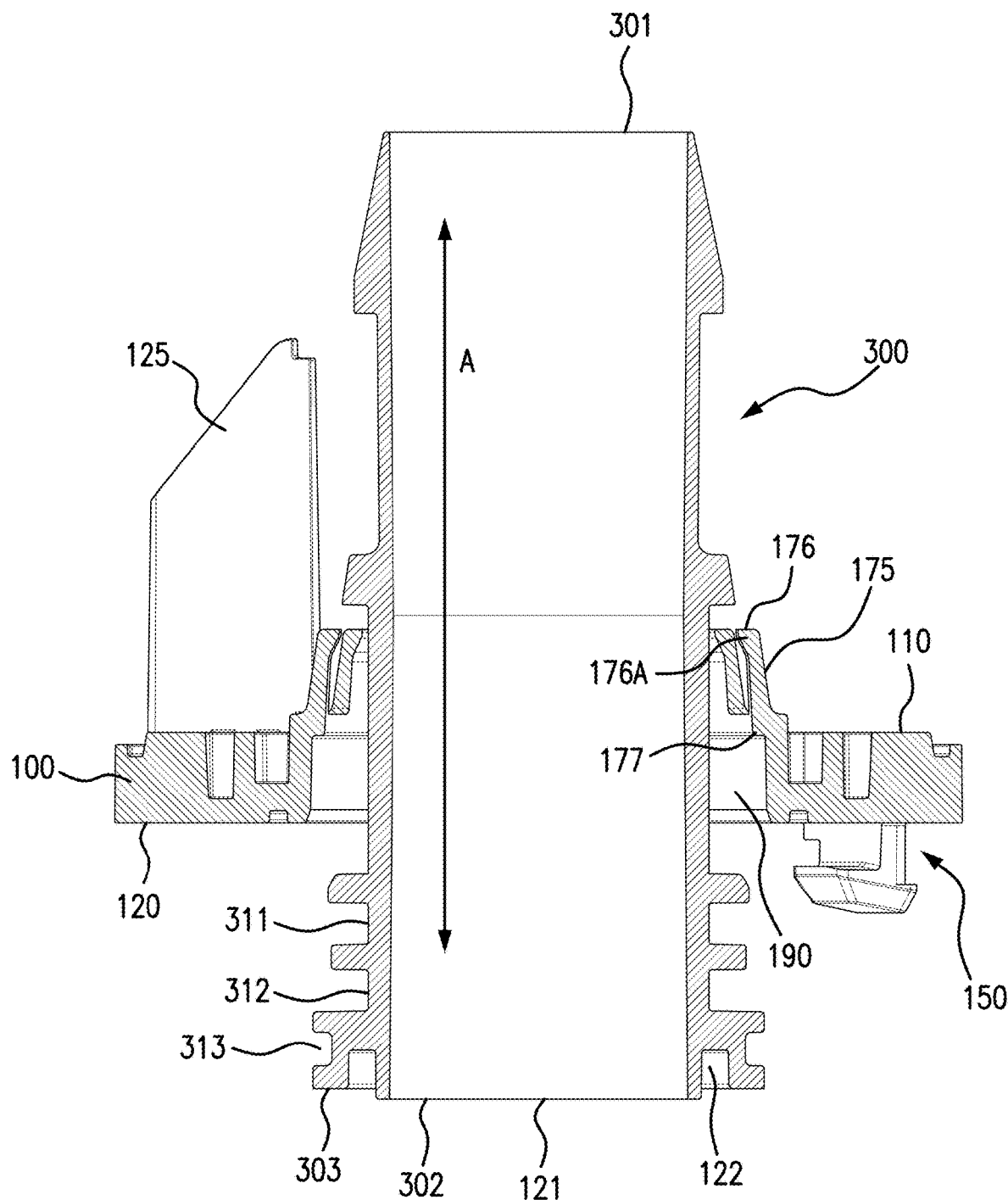
FIG. 2A is a drawing showing a cross-sectional view of the connector shown in FIG. 1, before the hollow tube is fully inserted in the hollow connector body.
Figure 2B:
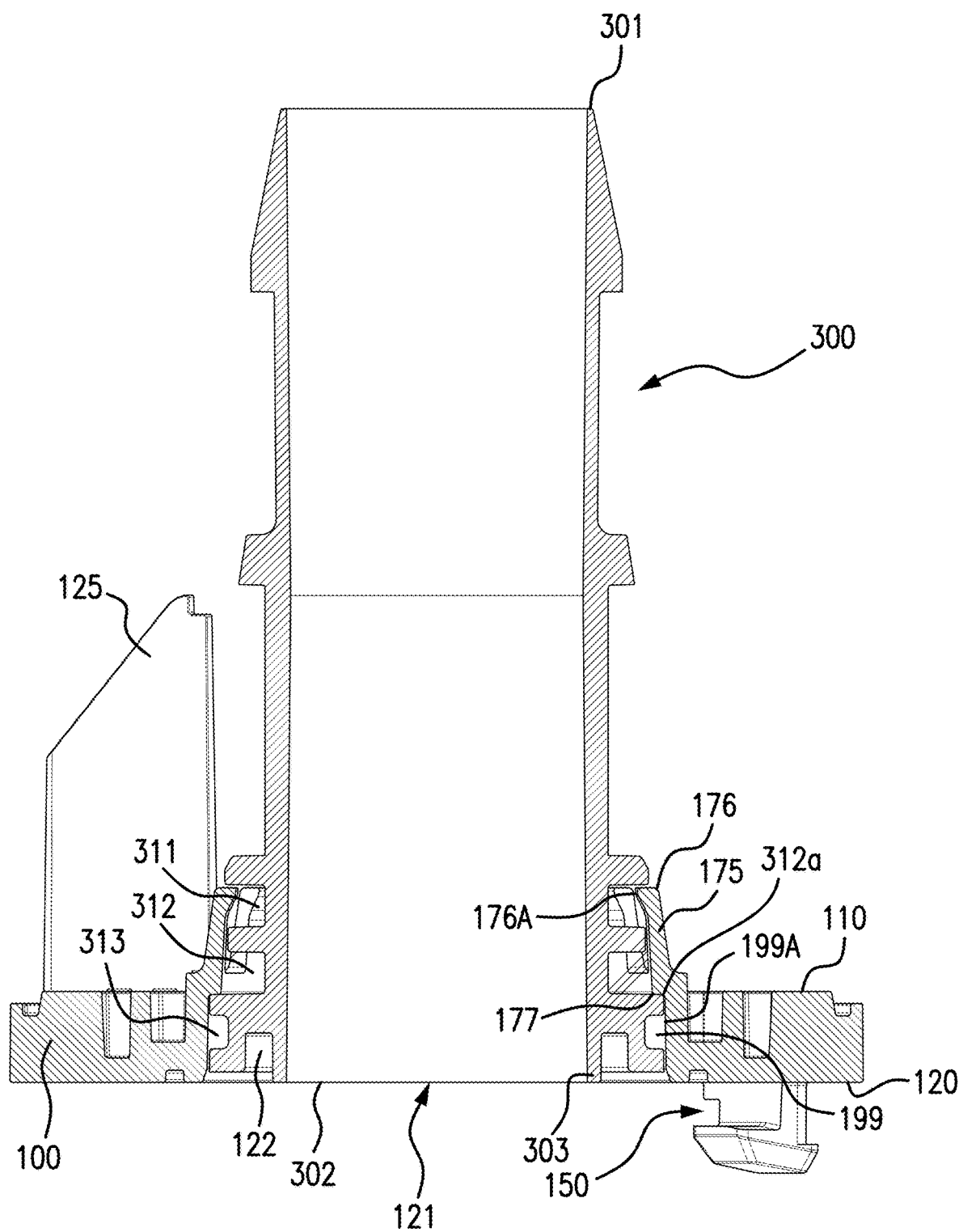
FIG. 2B is a drawing showing the hollow tube fully inserted in the hollow connector body.
Figure 3A:
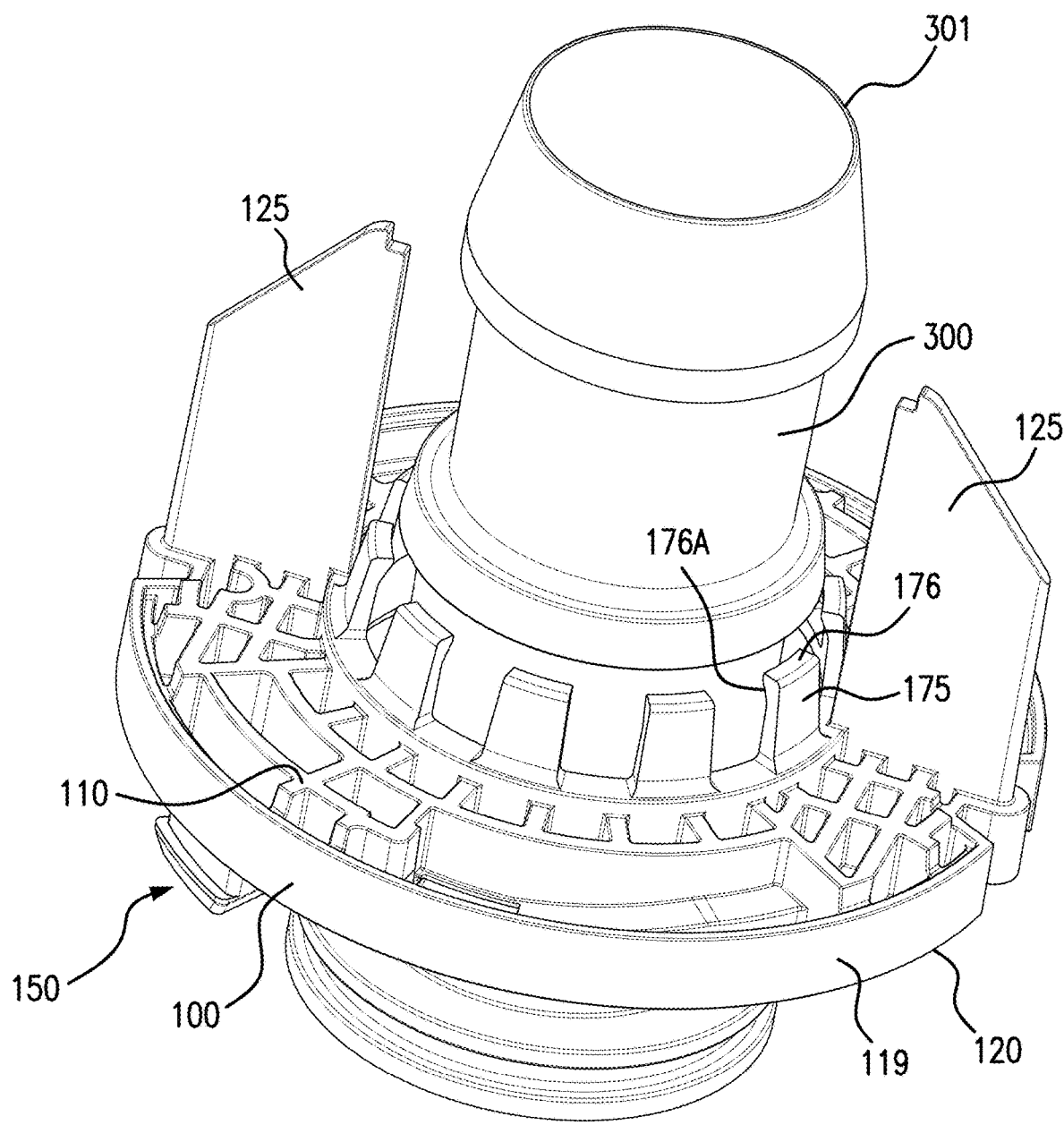
FIG. 3A is a drawing showing a top perspective view of the connector shown in FIG. 1, before the hollow tube is fully inserted in the hollow connector body.
Figure 3B:
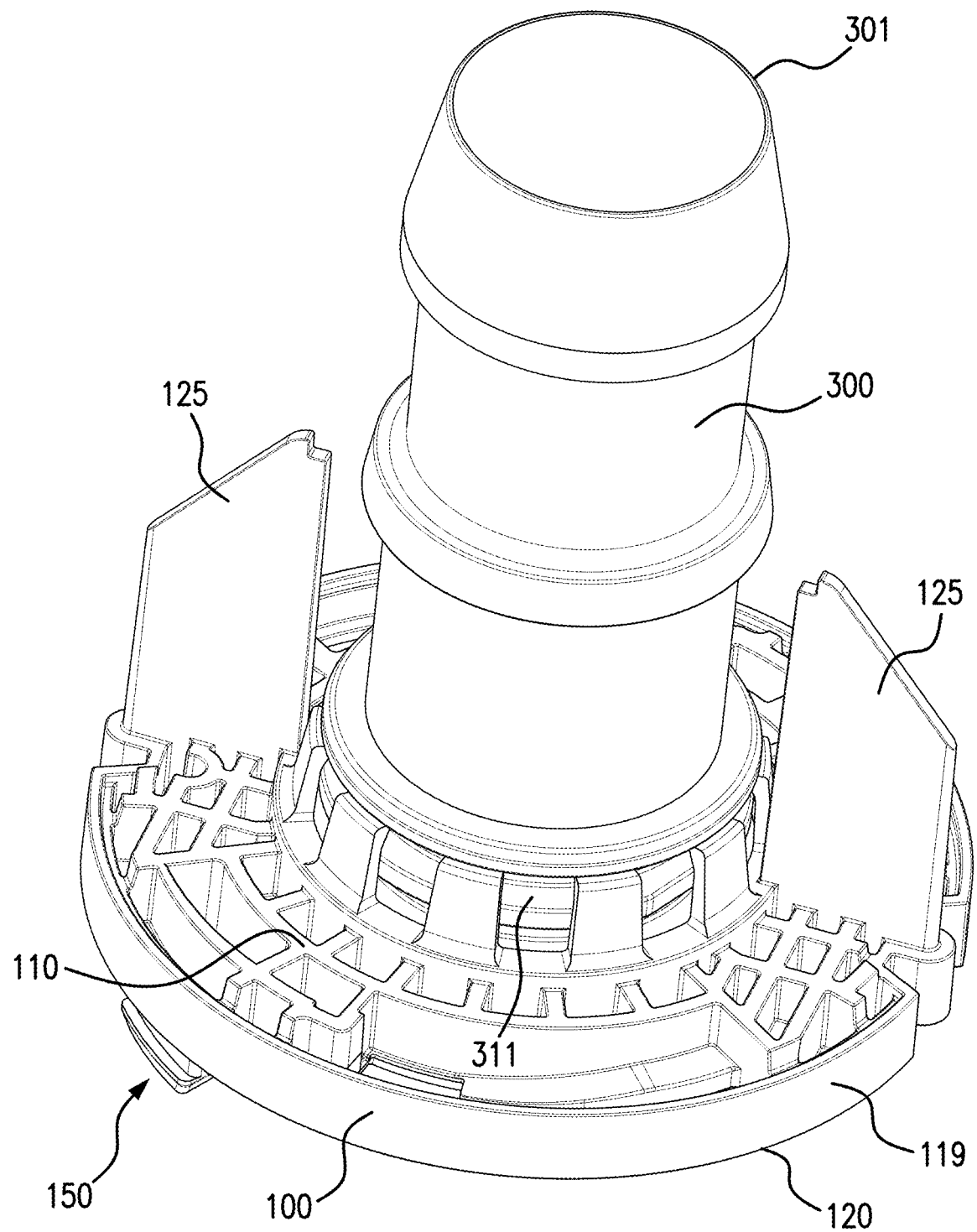
FIG. 3B is a drawing showing the hollow tube fully inserted in the hollow connector body.
Figure 4:
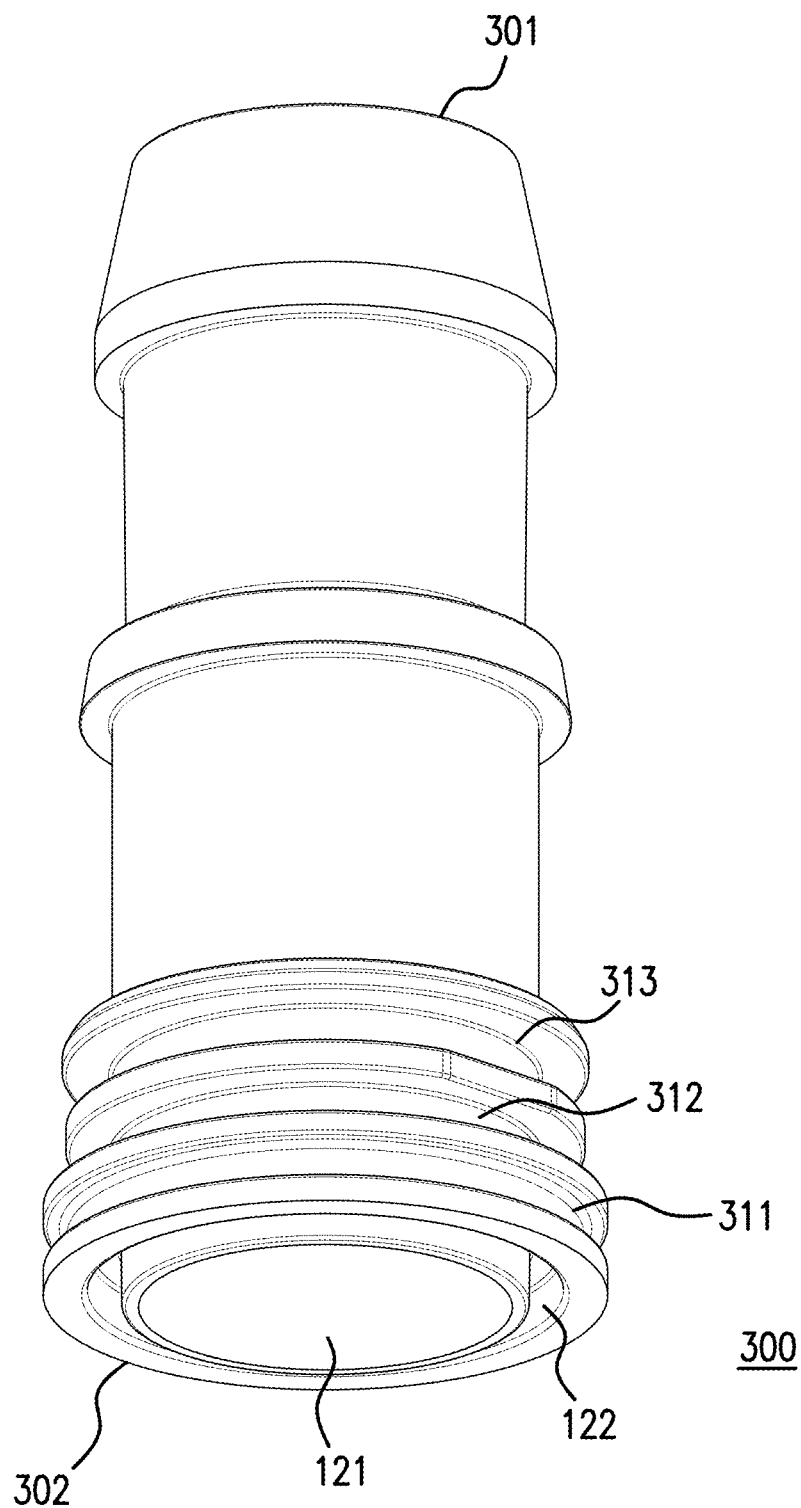
FIG. 4 is a drawing showing a perspective view of the hollow tube.
Figure 6A:
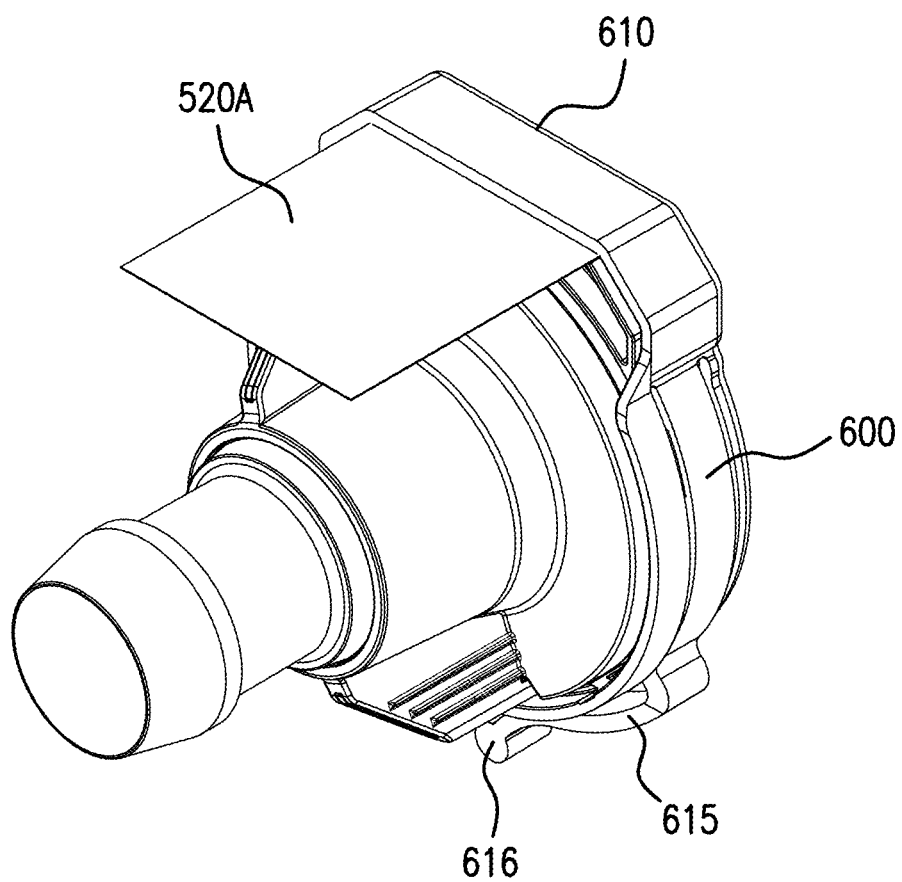
Figure 6B:
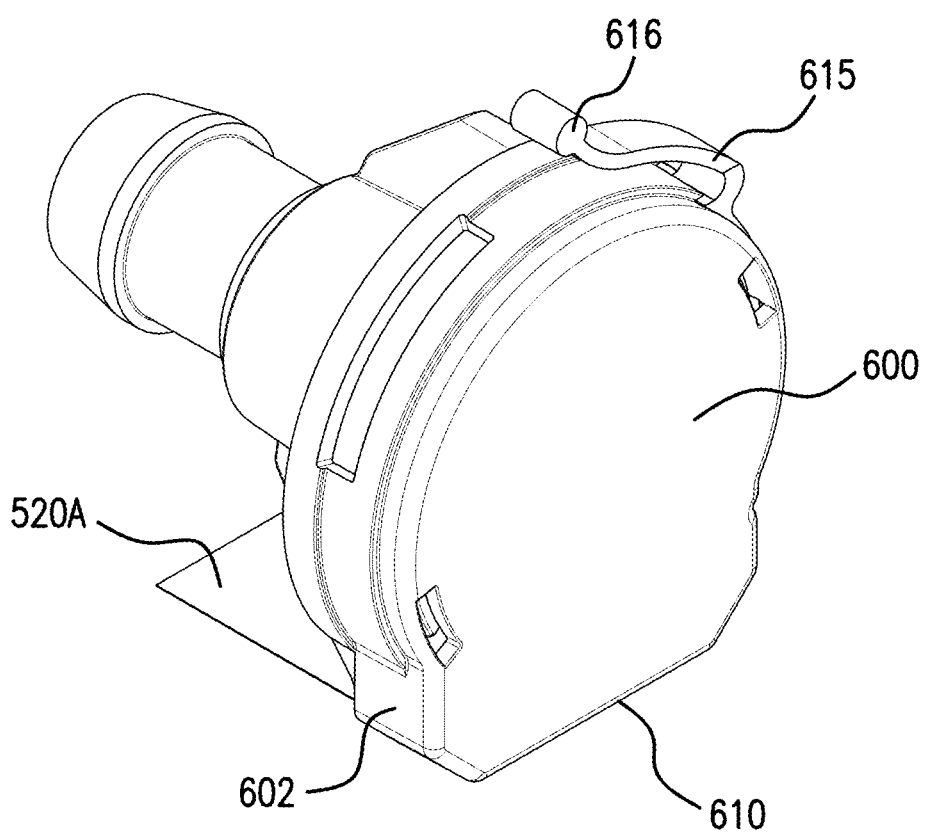

FIG. 6A is a drawing showing a front perspective view of the connector shown in FIG. 1, assembled; FIG. 6B is a drawing showing the rear perspective view of the assembled connector.

Figure 7A:
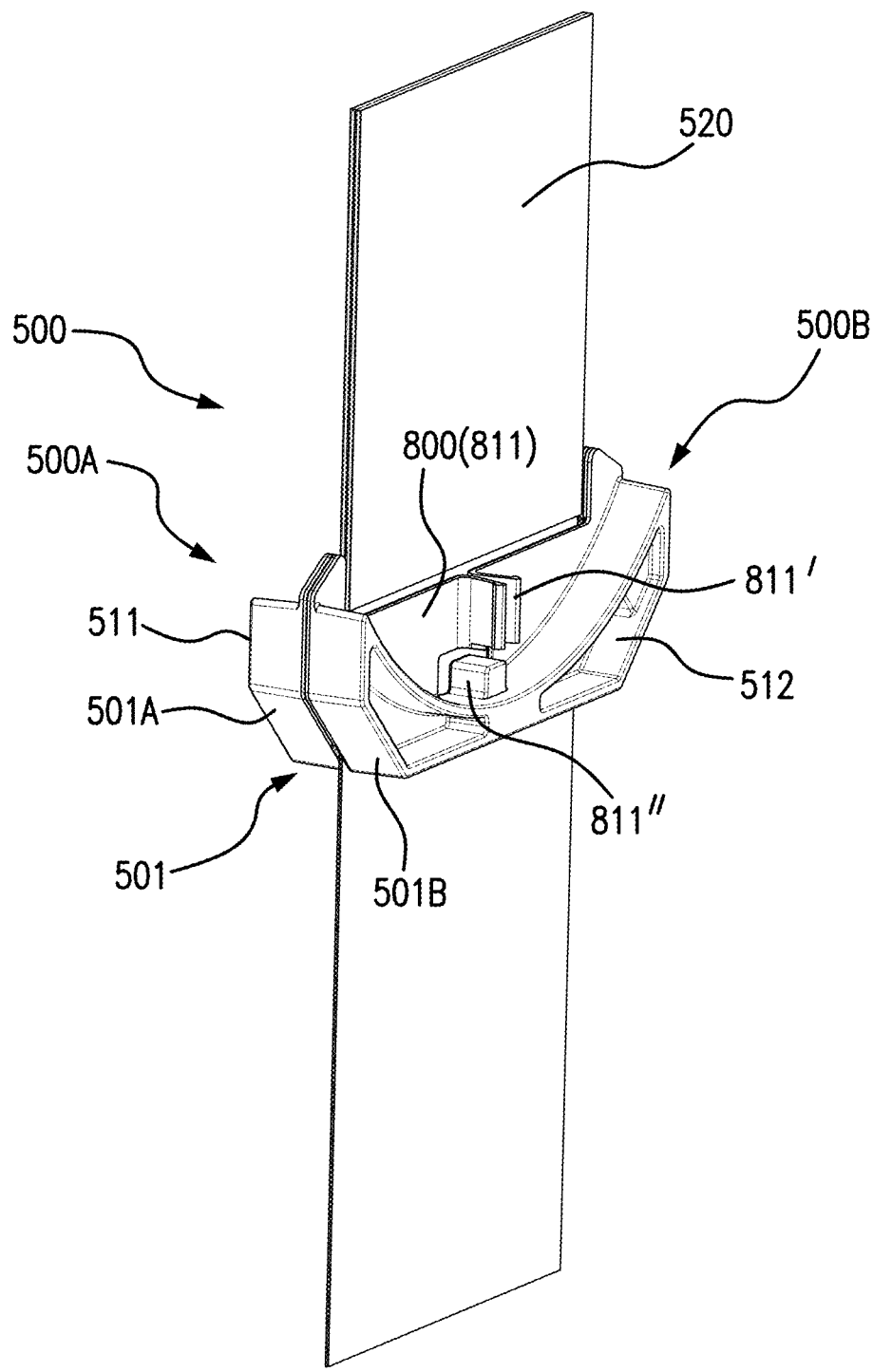
Figure 7B:
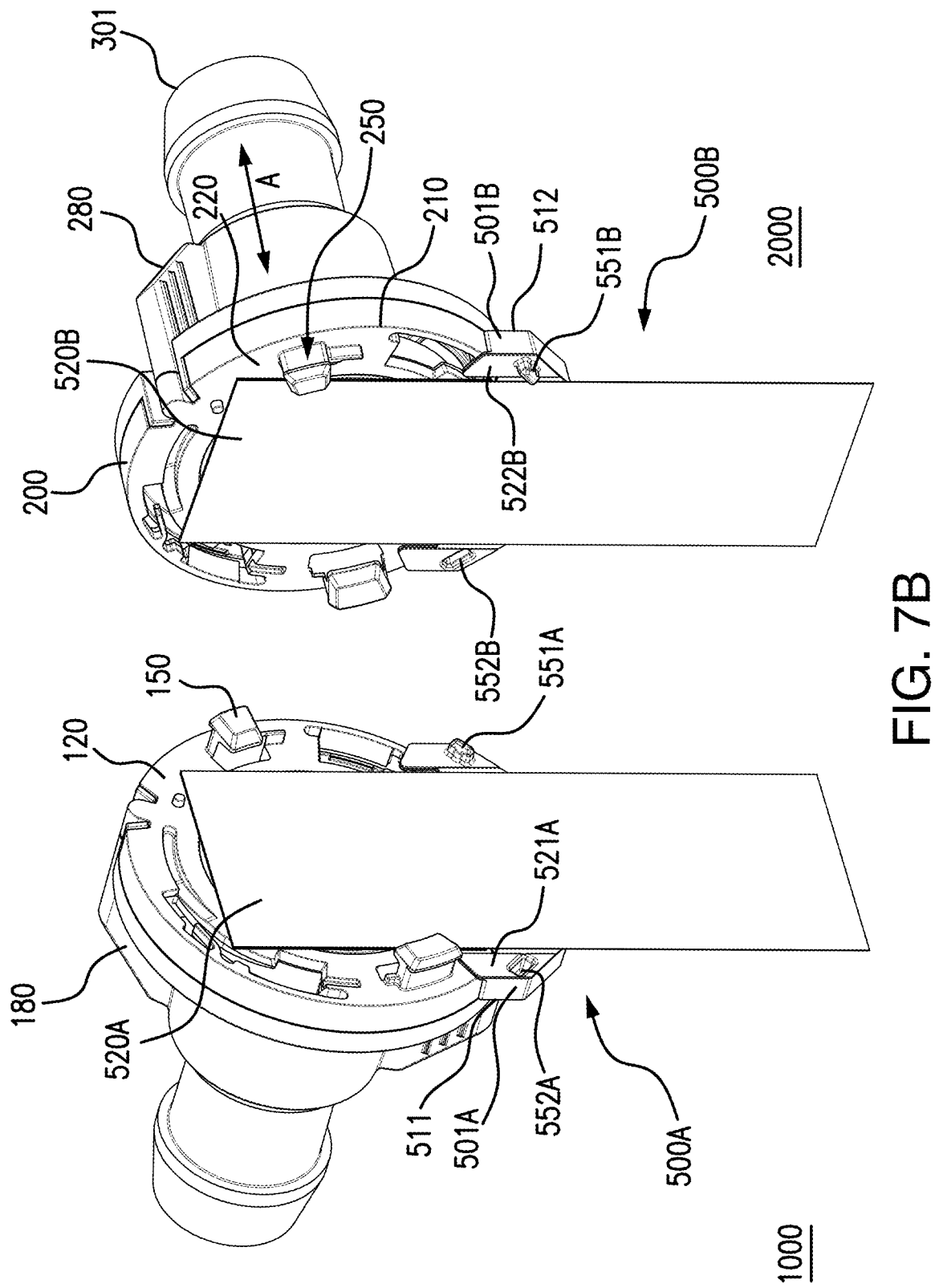

FIG. 7A is a drawing showing a perspective view of the anti-actuation subassembly of the anti-actuation assembly comprising a tab and a peelable strip in the connector assembly shown in FIG. 1, also showing another subassembly of the anti-actuation assembly used when first and second connector assemblies are connected; FIG. 7B is a drawing showing first and second anti-actuation subassemblies engaged with respective separate first and second hollow connector bodies (of separate first and second connector assemblies), wherein each subassembly includes a subassembly keying arrangement comprising a protrusion and a recess, allowing the subassemblies to be mated together when the first and second connector assemblies contact each other in a first position, before the first and second connector assemblies are subsequently twisted together, such that the first resilient deformable seal seals against the first hollow connector body, and the second resilient deformable seal seals against the second hollow connector body, in a second position, the second position comprising an actuation position.

Figure 8B:
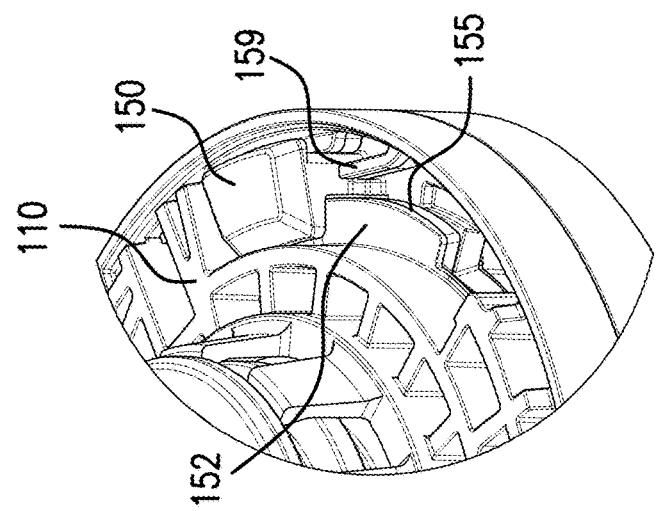
Figure 8A:
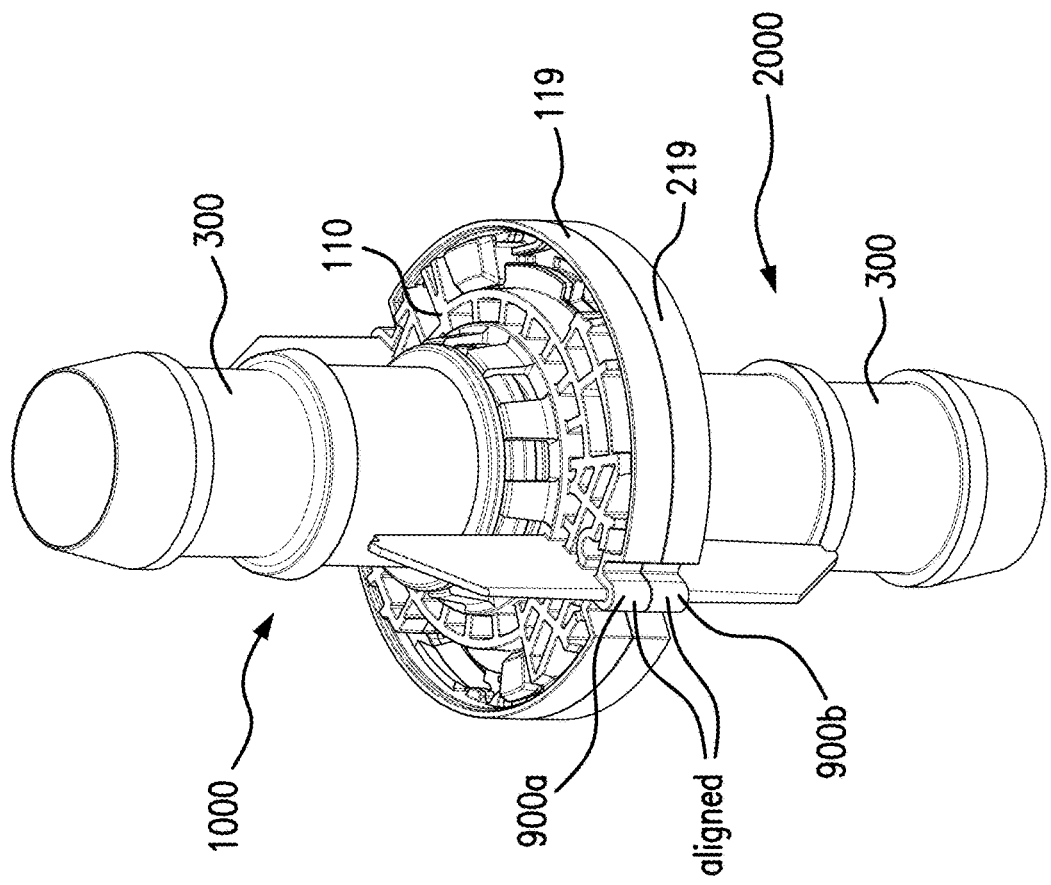

FIG. 8A is a drawing showing a perspective view of a connector assembly (without body covers) showing a ramp of the locking mechanism of one hollow connector body engages with the slot in the lug of the locking mechanism of the other hollow connector body; FIG. 8B is an enlarged partial perspective view of the connector assembly shown in FIG. 8A, showing one hollow connector body's locking mechanism comprising a ramp engaging with the slot in the lug in the other hollow connector body's locking mechanism as at least one of the connector bodies moves from the first position to the second position.

DETAILED DESCRIPTION OF THE INVENTION

In accordance with an aspect of the invention, a connector is provided comprising (a) a hollow connector body having a bottom face and an inner wall forming a central aperture, the central aperture passing through the bottom face; the inner wall having at least two resilient fingers, each of the at least two resilient fingers having an upper tip with an inwardly facing projection; and (b) a hollow tube retained in the central aperture, the hollow tube having a first open end, a second open end, and a longitudinal axis, the second end having a lower face including a central aperture and including a lower face annular groove including a resilient deformable annular seal arranged in the lower face annular groove surrounding the central aperture; the hollow tube including at least upper, middle, and lower grooves spaced apart along the longitudinal axis, the lower groove including a second resilient annular seal arranged in the lower groove, sealing against a portion of the inner wall of the hollow connector body; wherein the inwardly facing projections of the at least two resilient fingers of the hollow connector body are inserted in the upper groove of the hollow tube such that the hollow tube is rotatable within the central aperture without rotating the hollow connector body.

In an aspect of the connector, each of the resilient fingers includes an inwardly facing shoulder a distance from the upper tip, in a preferred aspect, the middle groove has a lower wall contacting the inwardly facing shoulder on each of the at least two resilient fingers.

In some aspects, the resilient annular seal arranged in the lower face annular groove has a flexible lip.

In another aspect, a connector assembly comprises an aspect of the connector, wherein, the bottom face of the hollow connector body (preferably, the bottom face is aligned with the second end lower face of the hollow tube), includes an integrally formed locking mechanism, the integrally formed locking mechanism comprising at least one lug including a slot, and at least one ramp; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the hollow connector body; and, a removable cap, engaged with the hollow connector body, wherein the removable anti-actuation assembly is interposed between the removable cap and the hollow connector body, the removable cap covering the bottom face of the hollow connector body.

In accordance with yet another aspect of the invention, a method for making fluid connections is provided, the method comprising (a) placing a bottom face of a first hollow connector body of a first connector assembly comprising a first rotatable hollow tube including a resilient deformable annular seal arranged in an annular groove, wherein the first rotatable hollow tube is retained in a central aperture of the first hollow connector body, wherein the bottom face of the first hollow connector body further comprises a first locking mechanism integrally formed with the bottom face of the first hollow connector body, the first locking mechanism comprising at least one lug including a slot, and at least one ramp, in contact with a bottom face of a second hollow connector body of a second connector assembly comprising a second rotatable hollow tube including a second resilient deformable annular seal arranged in an annular groove, wherein the second rotatable hollow tube is retained in a central aperture of the second hollow connector body, wherein the bottom face of the second hollow connector body further comprises a second locking mechanism integrally formed with the bottom face of the second hollow connector body, the second locking mechanism comprising at least one lug including a slot, and at least one ramp; in a first position; and (b) twisting the first hollow connector body and/or the second hollow connector body such that the first locking mechanism engages with the second locking mechanism, the first resilient deformable seal seals against the first hollow tube in the annular groove surrounding the central aperture of the first follow connector body, and the second resilient deformable seal seals against the second hollow tube in the annular groove surrounding the central aperture of the second hollow connector body, in a second position, the second position comprising an actuation position.

Aspects of the method can further comprise removing an anti-actuation assembly comprising at least one peel strip (preferably two peel strips), interposed between a first hollow connector body bottom face and the second hollow connector first body bottom face, after (a) (the first position) and before (b) (the second position).

In another aspect, a method of processing fluid is provided, comprising (a) placing a bottom face of a first hollow connector body of a first connector assembly comprising a first rotatable hollow tube including a resilient deformable annular seal arranged in an annular groove, wherein the first rotatable hollow tube is retained in a central aperture of the first hollow connector body, wherein the bottom face of the first hollow connector body further comprises a first locking mechanism integrally formed with the bottom face of the first hollow connector body, the first locking mechanism comprising at least one lug including a slot, and at least one ramp, in contact with a bottom face of a second hollow connector body of a second connector assembly comprising a second rotatable hollow tube including a second resilient deformable annular seal arranged in an annular groove, wherein the second rotatable hollow tube is retained in a central aperture of the second hollow connector body, wherein the bottom face of the second hollow connector body further comprises a second locking mechanism integrally formed with the bottom face of the second hollow connector body, the second locking mechanism comprising at least one lug including a slot, and at least one ramp; in a first position; and (b) twisting the first hollow connector body and/or the second hollow connector body such that the first locking mechanism engages with the second locking mechanism, the first resilient deformable seal seals against the first hollow tube in the annular groove surrounding the central aperture of the first follow connector body, and the second resilient deformable seal seals against the second hollow tube in the annular groove surrounding the central aperture of the second hollow connector body, in a second position, the second position comprising an actuation position; and passing fluid through the first and second connector assemblies.

If desired, the anti-actuation assembly comprises a first anti-actuation subassembly comprising the first surface of the anti-actuation assembly, and a first peel strip; and, a second anti-actuation subassembly comprising the second surface of the anti-actuation assembly, and a second peel strip. In some aspects, the first anti-actuation subassembly and the second anti-actuation subassembly are mated together when the first hollow connector body and the second hollow connector body contact each other in the first position.

Advantageously, even when using conduits having large diameters (e.g., ¾ inches are larger) and/or braiding such that the conduits are stiff and inflexible, since the hollow tubes can be rotated independent of the hollow connector bodies, fluid connections can be made independent of the orientation of the device which the connector is connected to.

Aspects of the invention are particularly suitable for single use technology (SUT) applications. Preferably, the connector assembly is a genderless connector assembly, i.e., not requiring male and female connections. Advantageously, a connector assembly can be connected to another connector assembly, for example, a connector assembly as described herein, or as described in U.S. Pat. No. 10,247,342.

Each of the components of the invention will now be described in more detail below, wherein like components have like reference numbers.

Using the aspect shown in FIG. 1 for reference, the connector assembly 1000 comprises a hollow connector body 100 wherein connector body 100 has top and bottom faces 110, 120, a rim 119, and a central aperture 190 passing through the top and bottom faces, and a rotatable hollow tube 300 retained in the central aperture, the hollow tube having a longitudinal axis A, a tube body extending from a first open end 301 to a second open end 302, the second open end having a lower face 303 including a tube central aperture 121, including a resilient deformable annular seal 130 having a central opening 131 and an outer flexible lip 132, wherein the seal 130 is arranged in an annular groove 122 in the tube lower face concentrically surrounding the tube central aperture 121.

In the aspects shown in FIGS. 1, 2A-2B, 3A-3B, and 5A, the hollow connector body 100 has an inner wall 199 forming a central aperture 190, the central aperture passing from the top face through the bottom face; the inner wall having a plurality of resilient fingers 175, each of the resilient fingers having an upper tip 176 with an inwardly facing projection 176A. In these illustrated aspects, each of the resilient fingers includes an inwardly facing shoulder 177 a distance from the upper tip, the shoulder contacting a portion of the lower surface 312a of the tube middle groove 312, assisting in preventing downward movement of the tube once fully inserted in the hollow connector body (see, FIG. 2B). In those aspects including shoulders, the distance of the shoulders from the upper tips can be determined by one of skill in the art.

If desired, the top face of the connector body may include one or more blades 125 for insertion into slots in a cover 180.

In the aspects shown in FIGS. 1, 2A-2B, 3A-3B, and 4, the hollow tube 300 includes at least upper 311, middle 312, and lower 313 grooves spaced apart along the longitudinal axis, the lower groove including a second resilient annular seal 313A arranged in the lower groove, sealing against a portion 199A of the inner wall 199 of the hollow connector body (see, FIG. 2B); wherein the inwardly facing projections of the resilient fingers of the hollow connector body are inserted in the upper groove of the hollow tube (see, FIGS. 2A-2B, 3A-3B) such that the hollow tube is rotatable within the central aperture without rotating the hollow connector body. In the aspect illustrated in FIG. 2B, the middle groove 312 has lower surface 312a contacted by the shoulders 177. The inserted projections, similar those aspects including shoulders 177 contacting surface 312a, assist in preventing downward movement of the tube once fully inserted in the hollow connector body, and the inserted projections and shoulders still allow the hollow tube to be rotatable within the central aperture without rotating the hollow connector body.

The bottom face 120 of the connector body 100 includes a locking mechanism 150. In some aspects, first and second connector assemblies 1000, 2000 have identical structures and are coupled to each other by respective identical locking mechanisms (see, for example, FIGS. 8A and 8B). However, in other aspects, a connector assembly according to an aspect of the invention can be coupled to a different connector assembly, e.g., as disclosed in U.S. Pat. No. 10,247, 342.

Illustratively, with respect to identical structures, the connector assembly 2000 comprises a hollow connector body 200 wherein connector body 200 has top and bottom faces 210, 220, a rim 219, and a central aperture 290, and a rotatable hollow tube 300 retained in the aperture, the hollow tube having a longitudinal axis A, a first open end 301, a second open end 302 having a lower face 303 including a tube central aperture 221, including a resilient deformable annular seal 230 having a central opening 231 and an outer flexible lip 232, wherein the seal 230 is arranged in an annular groove 222 in the tube lower face concentrically surrounding the tube central aperture 221.

The connector bodies 100, 200 may be coupled to one another at their bottom faces 120, 220 by (using FIG. 5B for reference) respective locking mechanisms (first locking mechanism 150; second locking mechanism 250), the respective locking mechanisms comprising a lug 151, 251 extending above the face, the lug including a slot 152, 252, and a guide 153, 253, a recess 154, 254; and a ramp 155, 255 extending below the face. In some embodiments, the locking mechanisms each include a guide 153, 253 on a lug, and an arm 159, 259. In the embodiment illustrated in FIG. 5B, the first connector body 100 includes first locking mechanisms 150A, 150B, including lugs 151A, 151B, slots 152A, 152B, guide 153A, recess 154A, ramps 155A, 155B, and arms 159A, 159B; and the second connector body includes second locking mechanisms 250A, 250B, including lugs 251A, 251B, slots 252A, 252B, guide 253A, recess 254A, ramps 255A, 255B, and arms 259A, 259B. The locking mechanisms are integrally formed with the bodies, and as such, does not move separately from the rest of the body when the body moves from the first contact position to the second contact (actuation) position.

As will be discussed in more detail below after an anti-actuation assembly 500 is removed, either or both of the hollow connector bodies can be rotated from a first contacting position such that the ramp(s) of the locking mechanism(s) of one hollow connector body engages with the slot(s) in the lug(s) of the locking mechanism(s) of the other hollow connector body, until the hollow bodies are in a second contacting (actuation (or activating)) position. In a preferred aspect, after the second contacting position is provided, fluid is processed by passing the fluid through the first and second hollow connector bodies.

The hollow connector bodies can be coupled to each other, including using the locking mechanisms and rotation from the first contacting position to the second contacting (actuation) position, as disclosed in U.S. Pat. No. 10,247,342.

Once the bodies are in the actuation position, the interiors of the connector bodies fluidly communicate with one another through the coaxially aligned apertures 121,221, preferably, in a sterile manner free of any external contamination.

Optionally, and as shown in FIGS. 8A and 8B, (a) the surface of the ramp and the surface of the slot that will contact the surface of the ramp have initial angles, and then level, such that the lugs stop on a level surface, providing a desired amount of pressure on the main bodies of the seals, when the connector bodies are in the actuation position, and/or (b), as shown particularly in FIG. 5B, the locking mechanism has an arm 159 (159A, 159B), 259 (259A, 259B) that locks the lug guide 153 (153A), 253 (253A) into the recess 154 (154A), 254 (254A) once the lug has passed, retaining the lug in the actuation position, to prevent disconnection.

The embodiment of the connector assembly 1000 shown in FIG. 1 also includes a removable anti-actuation assembly 500 comprising a tab 501 having a first surface 511 (facing the first hollow connector first body end) and a second surface 512 (facing the second hollow connector first body end), and a peel strip 520, interposed between the first hollow connector first body end and the second hollow connector first body end, wherein, when the first hollow connector body and the second hollow connector body contact each other in the first position, the anti-actuation assembly, when present, prevents forming the actuation position of the connector assembly, and when removed, allows forming the actuation position of the connector assembly. If desired, the tab can include a pull ring.

In some aspects, the integrally formed locking mechanism and anti-actuation assemblies and their operation can be as described in U.S. Pat. No. 10,247,342.

If desired, the connector assembly can comprise an alignment arrangement for mating the anti-actuation assembly with the first connector hollow body and the second hollow connector body, the alignment arrangement comprising protrusions and recesses; wherein the first and second surfaces of the anti-actuation assembly, the first hollow connector bottom face, and the second hollow connector bottom face each have at least one protrusion and/or at least one recess, such that the first surface of the anti-actuation assembly mates with the first hollow connector first body end, and the second surface of the anti-actuation assembly mates with the second hollow connector first body end.

For example, in the aspect shown in FIGS. 5B, 5C, 7A, and 7B, the connector further comprises an alignment arrangement 800, including a recess 801 in the outer face of the first hollow connector body (illustrated recess shown with 2 slots, 801a, 801b), and a protrusion 810 (shown as having 2 snap hooks 810' and a pin 810") on the first surface 511 of the anti-actuation tab 501, the protrusion being engageable with the recess 801 (wherein the second connector hollow body has the same structure). In aspects including pins, the engagement of the pins with the recesses further reduces flexing/movement when the subassemblies are engaged with the respective hollow bodies.

In some aspects, e.g., as shown in FIGS. 5B, 5C, 7A, and 7B, anti-actuation assembly 500 comprises first anti-actuation subassembly 500A comprising a subassembly tab 501A including the first surface 511, and a first peel strip 520A; and, a second anti-actuation subassembly 500B comprising a subassembly tab 501B including the second surface 512, and a second peel strip 520B. If desired, each subassembly can comprise a keying arrangement comprising at least one protrusion and at least one recess so that the first anti-actuation subassembly and the second anti-actuation subassembly can be mated together when the first hollow connector body and the second hollow connector body contact each other in the first position. For example, as shown in FIG. 5C, subassembly tab 501A has a second surface 521A including a keying arrangement 550A comprising a protrusion 551A and a recess 552A, and subassembly tab 501B has a second surface 522B including a keying arrangement 550B comprising a protrusion 551B and a recess 552B, wherein protrusion 551A can be mated with recess 552B, and protrusion 551B and be mated with recess 551A. Advantageously, this allows the operator to pull either or both tabs 501A, 501B and/or either or both peelable strips 520A, 520B and remove the anti-actuation assembly from the connector assembly, so that the hollow connector bodies can be placed in the actuation position.

To enhance the sterility of the interiors of the connector bodies, peel strips (seal layers) are preferably arranged to cover the openings at the first ends of the connector bodies. The peel strips may be variously configured. Typically, the peel strip(s) are joined (e.g., welded, trapped, or clamped) to the anti-actuation assembly tab(s) and/or the faces of the hollow connector bodies. Preferably, peel strips are joined to the respective subassembly tabs and the hollow connector body faces (also covering the seals and contacting the seal lips). For many embodiments, the peel strip(s) may also cover all or at least a portion of the face seals without being joined to the seals. For example, each peel strip may completely cover at least the seal closest to the openings. The peel strip may not be joined to the seals themselves but may be joined to the surface of the face surrounding each seal.

The peel strip may be made from an impermeable material or a permeable material that resists the passage of contaminants, including biological containments. These materials include, but are not limited to, elastomeric sheets, polymeric films, and metal foils, e.g., aluminum foil, any of which may further include a reinforcing material. Further, the peel strip may be coated and/or impregnated with a biocide. Preferably, the peel strip is a sterile porous or microporous membrane, allowing steam to pass through during autoclaving, in some aspects having a minimum tensile strength of about 60N.

Any of numerous seals may be provided on the face, including, for example, gaskets, resilient sealing members, or O rings. Preferably, the seal comprises a soft rubber or thermoplastic elastomer (TPE) (e.g., about 50 to about 65 shore A). Preferably, the seals can include flexible seal lips that assist in preventing environmental contamination from entering the connector assembly when the anti-actuation assembly is removed. Since the lips can flex and spring, the peel strips can be removed with reduced force, and the lips quickly close the gap. As the hollow bodies are moved (e.g., twisted) into the actuation position, the flexible lips (that are preferably narrow) can quickly fold out of the way into an optional recess in each hollow tube, wherein both the lips and the seal bodies (seal lozenges) contact each other, providing a more robust face seal, and the contact between the lozenges provides a face to face seal, preventing fluid leaks even under increases pressures (e.g., pressures up to about 4 barg).

If desired, the first hollow connector body can comprises a first connector external surface (e.g., as part of a cover 180 and/or rim 119 (see, FIGS. 1 and 8A) on the first hollow connector body) further comprising a first external connector alignment indicator 900*a*; and the second hollow connector body comprises a second connector external surface (e.g., as part of a cover 280 and/or rim 219 (see, FIG. 8A) on the second hollow connector body) further comprising a second external alignment indicator 900*b*; the first external alignment indicator and the second external alignment indicator not aligning when the first hollow connector body and the second hollow connector body are in the first position, and the first alignment indicator and the second alignment indicator aligning when the first hollow connector body and the second hollow connector body are in the second (actuation) position.

To prevent inadvertent removal of or damage to the peel strips, each connector body may further comprise a removable cap which covers at least a substantial portion of the peel strip and the first end of the connector body. The cap can be fitted to the connector body at the first end, for example, by a friction fit or a snap fit, and may have any of a wide variety of configurations. For example, as shown in FIGS. 1, 6A, 6B, and 7B, each cap 600 (cap 700 on the second connector assembly will have the same structures) may have a rigid top 601 which protects at least part of the peel strip and a skirt 602 which fits along the rim 119 of the connector body 100. The cap 600 may also include handle 610 as part of the skirt, or which extends axially below the skirt 602. Preferably, as shown in FIGS. 1 and 6B, the cap includes a tear strip 615 having a tear strip handle 616 allowing the operator to grasp the tear strip handle and tear the tear strip, allowing the cap to be more easily removed from the connector body. The peel strip 520 (520A) may be bent axially under the handle 610 and the handle may extend along all or at least a portion of the peal strip 520 (520A). The handle, tear strip, and/or tear strip handled may be used to lift the cap 600 off of the connector body 100 and may also prevent inadvertent manipulation of the anti-actuation assembly tab 501 and/or peel strip.

The components of the connector assembly can be sterilized as is known in the art (e.g., autoclaved, gamma irradiated, etc.)

The components of the connector assembly may be formed from a wide variety of materials. For example, one or more of any one of the following: hollow connector body, hollow tube, connector body cover, locking mechanism, tab, and cap, may be made from any metallic material and/or polymeric material which is compatible with the fluid that will flow through the connector assembly. Preferably, the connector bodies, hollow tubes, the locking mechanisms, and the caps are made from polymeric material, and the polymeric material may include, but is not limited to, one or more of a polycarbonate, polypropylene, polystyrene, polyvinyl chloride, polyethersulphone, polyvinylidene fluoride, or polysulphone. For some embodiments, a transparent or translucent polymeric material may be selected. Typically, the hollow bodies, hollow tubes, tabs, and connector body covers are formed from a rigid injection molded plastic, preferably a BPA-free plastic, such as polyethersulfone (PES), polycarbonate (PC), polysulfone (PSU), and polybutylene terephthalate (PBT), and the cap is made from a low density injection molded plastic such as TPE or polypropylene (PP).

The components may be fabricated in a variety of ways, including molding, machining, pressing, and stamping, and may be fashioned into subassemblies.

Additionally, or alternatively, some components according to aspects of the invention can be monolithic, for example, manufactured via additive manufacturing (sometimes referred to as "additive layer manufacturing" or "3D printing"). They are typically formed by repeated depositions of a metal powder bound together with an activatable binder (e.g., binder jetting, sometimes referred to as "drop on powder"), typically followed by agglomerating the powder, e.g., by sintering. Some components can be manufactured together via additive manufacturing in a continuous operation at substantially the same time.

Any suitable additive manufacturing equipment can be used, and a variety of production 3D printers are suitable and commercially available.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A connector comprising
(a) a hollow connector body having a bottom face and an inner wall forming a central aperture, the central aperture passing through the bottom face; the inner wall having at least two resilient fingers, each of the at least two resilient fingers having an upper tip with an inwardly facing projection; and
(b) a hollow tube retained in the central aperture, the hollow tube having a first open end, a second open end, and a longitudinal axis, the second end having a lower face including a central aperture and including a lower face annular groove including a resilient deformable annular seal arranged in the lower face annular groove surrounding the central aperture; the hollow tube including at least upper, middle, and lower grooves spaced apart along the longitudinal axis, the lower groove including a second resilient annular seal arranged in the lower groove, sealing against a portion of the inner wall of the hollow connector body; wherein the inwardly facing projections of the at least two resilient fingers of the hollow connector body are inserted in the upper groove of the hollow tube such that the hollow tube is rotatable within the central aperture without rotating the hollow connector body.

2. The connector of claim 1, wherein the each of the at least two resilient fingers includes an inwardly facing shoulder a distance from the upper tip.

3. The connector of claim 2, wherein the middle groove has a lower wall contacting the inwardly facing shoulder on each of the at least two resilient fingers.

4. A connector assembly comprising the connector of claim 3, wherein the bottom face of the hollow connector body includes an integrally formed locking mechanism, the integrally formed locking mechanism comprising at least one lug including a slot, and at least one ramp; and an anti-actuation assembly engagement portion comprising at least one recess and/or at least one protrusion;
a removable anti-actuation assembly comprising at least one peel strip, and at least one recess and/or at least one protrusion, the at least one recess and/or at least one protrusion being engaged with the anti-actuation assembly engagement portion of the hollow connector body; and,
a removable cap, engaged with the hollow connector body, wherein the removable anti-actuation assembly is interposed between the removable cap and the hollow connector body, the removable cap covering the bottom face of the hollow connector body.

5. A connector assembly comprising the connector of claim 2, wherein the bottom face of the hollow connector body includes an integrally formed locking mechanism, the integrally formed locking mechanism comprising at least one lug including a slot, and at least one ramp; and an anti-actuation assembly engagement portion comprising at least one recess and/or at least one protrusion;
a removable anti-actuation assembly comprising at least one peel strip, and at least one recess and/or at least one protrusion, the at least one recess and/or at least one protrusion being engaged with the anti-actuation assembly engagement portion of the hollow connector body; and,
a removable cap, engaged with the hollow connector body, wherein the removable anti-actuation assembly is interposed between the removable cap and the hollow connector body, the removable cap covering the bottom face of the hollow connector body.

6. The connector of claim 1, wherein the middle groove has a lower wall contacting an inwardly facing shoulder on each of the at least two resilient fingers.

7. A connector assembly comprising the connector of claim 6, wherein the bottom face of the hollow connector body includes an integrally formed locking mechanism, the integrally formed locking mechanism comprising at least one lug including a slot, and at least one ramp; and an anti-actuation assembly engagement portion comprising at least one recess and/or at least one protrusion;
a removable anti-actuation assembly comprising at least one peel strip, and at least one recess and/or at least one protrusion, the at least one recess and/or at least one protrusion being engaged with the anti-actuation assembly engagement portion of the hollow connector body; and,
a removable cap, engaged with the hollow connector body, wherein the removable anti-actuation assembly is interposed between the removable cap and the hollow connector body, the removable cap covering the bottom face of the hollow connector body.

8. A connector assembly comprising the connector of claim 1, wherein the bottom face of the hollow connector body includes an integrally formed locking mechanism, the integrally formed locking mechanism comprising at least one lug including a slot, and at least one ramp; and an anti-actuation assembly engagement portion comprising at least one recess and/or at least one protrusion;
a removable anti-actuation assembly comprising at least one peel strip, and at least one recess and/or at least one protrusion, the at least one recess and/or at least one protrusion being engaged with the anti-actuation assembly engagement portion of the hollow connector body; and,
a removable cap, engaged with the hollow connector body, wherein the removable anti-actuation assembly is interposed between the removable cap and the hollow connector body, the removable cap covering the bottom face of the hollow connector body.

\* \* \* \* \*